(12) United States Patent  
Fruchey et al.

(10) Patent No.: US 11,099,144 B2  
(45) Date of Patent: Aug. 24, 2021

(54) LOW SULFUR FUEL WITH ADEQUATE COMBUSTION QUALITY

(71) Applicant: ExxonMobil Research and Engineering Company, Annandale, NJ (US)

(72) Inventors: Erin R. Fruchey, Philadelphia, PA (US); Suzanne R. Golisz, Annandale, NJ (US); Kenneth C. H. Kar, Philadelphia, PA (US); Sheryl B. Rubin-Pitel, Newtown, PA (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 0 days.

(21) Appl. No.: 16/716,941

(22) Filed: Dec. 17, 2019

(65) Prior Publication Data

US 2021/0024842 A1 Jan. 28, 2021

Related U.S. Application Data

(60) Provisional application No. 62/877,129, filed on Jul. 22, 2019.

(51) Int. Cl.
*G01N 25/48* (2006.01)
*G01N 33/28* (2006.01)
*C10L 1/04* (2006.01)

(52) U.S. Cl.
CPC ............ *G01N 25/4833* (2013.01); *C10L 1/04* (2013.01); *G01N 33/2811* (2013.01);
(Continued)

(58) Field of Classification Search
CPC ...... C10L 1/04; C10L 1/08; C10L 2200/0438; C10L 2270/026; C10L 2200/0263;
(Continued)

(56) References Cited

U.S. PATENT DOCUMENTS

2015/0240174 A1* 8/2015 Kraus ................. C10L 1/04  
585/13  
2017/0002279 A1* 1/2017 Brown ................. C10G 69/04  
(Continued)

FOREIGN PATENT DOCUMENTS

BR PI1101412 A2 * 1/2014  
JP 2013203802 A * 10/2013  
JP 5868754 B2 * 2/2016

OTHER PUBLICATIONS

SIA Nord Control Standards of Marine Distillate fuels and Gas Oils. www.nord-control.com/docs.html 1996 (Year: 1996).*
(Continued)

*Primary Examiner* — Latosha Hines  
(74) *Attorney, Agent, or Firm* — Robert A. Migliorini

(57) ABSTRACT

Fuel compositions that are low sulfur and have adequate combustion quality are disclosed. An example fuel composition that is low sulfur may have the following enumerated properties: a sulfur content of about 0.50% or less by weight of the fuel composition; a calculated carbon aromaticity index of about 870 or less; a density at 15° C. of about 900 kg/m³ to about 1,010 kg/m³; a kinematic viscosity at 50° C. of about 100 centistokes to about 700 centistokes; and an estimated cetane number of about 7 or greater.

19 Claims, 1 Drawing Sheet

(52) U.S. Cl.
CPC .. *G01N 33/2829* (2013.01); *C10L 2200/0263* (2013.01); *C10L 2200/0415* (2013.01); *C10L 2200/0461* (2013.01); *C10L 2270/02* (2013.01); *C10L 2290/543* (2013.01)

(58) Field of Classification Search
CPC ..... C10L 2200/0415; C10L 2200/0461; C10L 2270/02; C10L 2290/543; G01N 25/4833; G01N 33/2811; G01N 33/2829
See application file for complete search history.

(56) References Cited

U.S. PATENT DOCUMENTS

| | | |
|---|---|---|
| 2018/0230389 A1 | 8/2018 | Moore et al. |
| 2019/0040329 A1* | 2/2019 | Moore .................. C10G 69/04 |
| 2019/0127651 A1 | 5/2019 | Kar et al. |
| 2019/0185772 A1 | 6/2019 | Berkhous et al. |

OTHER PUBLICATIONS

"ISO 8217 2017 Fuel Standard for Marine Distillate Fuels", Jul. 8, 2019.
The International Search Report and Written Opinion of PCT/US2019/066762 dated Apr. 1, 2020.

* cited by examiner

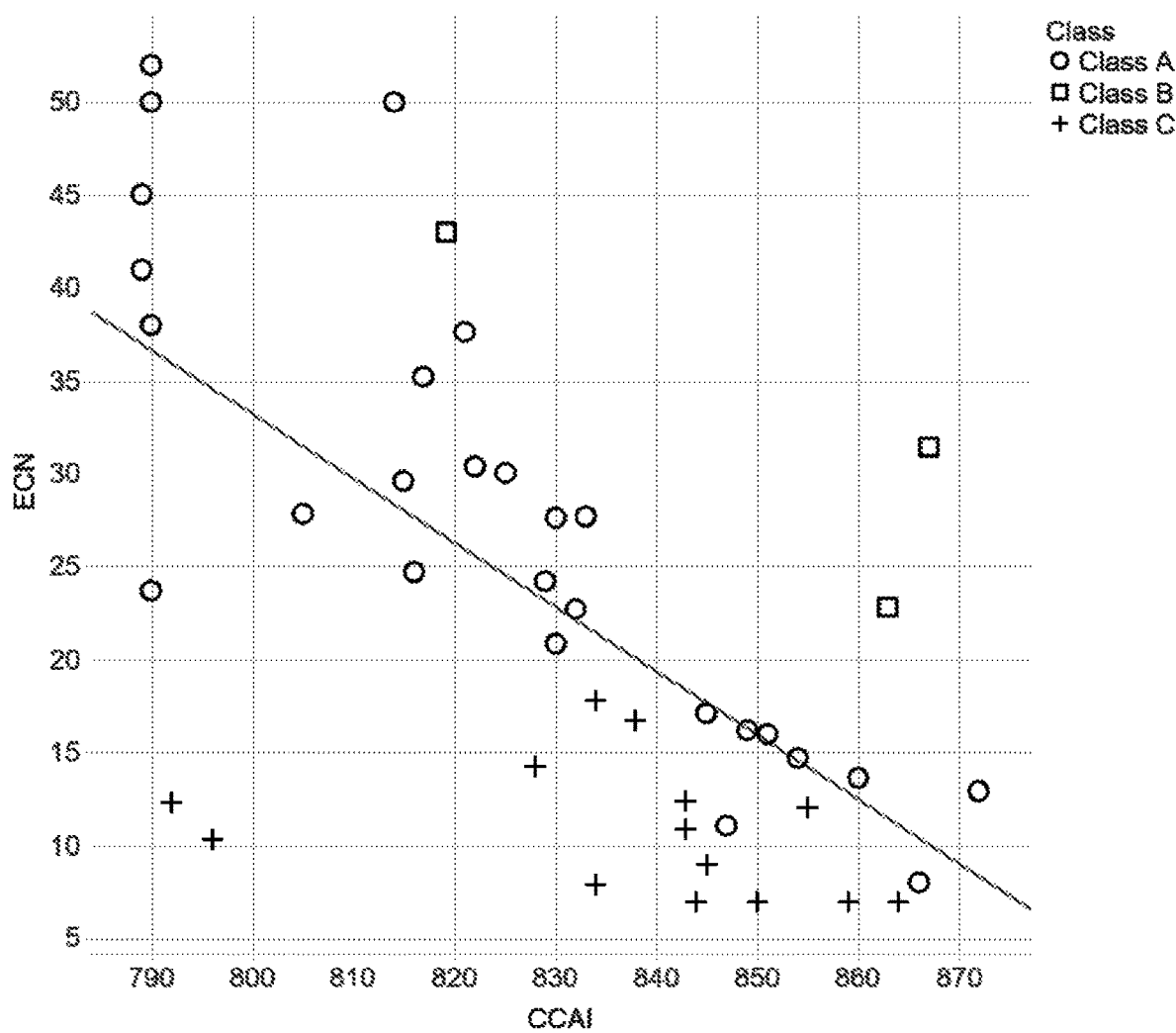

LOW SULFUR FUEL WITH ADEQUATE COMBUSTION QUALITY

CROSS REFERENCE TO RELATED APPLICATIONS

This application claims priority to U.S. Provisional Application Ser. No. 62/877,129 filed Jul. 22, 2019, which is herein incorporated by reference in its entirety.

STATEMENT OF RELATED APPLICATIONS

This application is related to Ser. No. 16/716,986 entitled "Prediction Of Fuel Oil Properties By Differential Scanning Calorimetry," having common inventors and assignee and filed on an even date herewith, the disclosure of which is incorporated by reference herein in its entirety.

FIELD

This application relates to fuel compositions and, more particularly, embodiments relate to fuel compositions that are low sulfur and have adequate combustion quality.

BACKGROUND

Internal combustion engines are a type of engine where combustion of a fuel composition occurs in a combustion chamber to transfer chemical energy into mechanical energy. One type of internal combustion engine is a compression ignition engine in which ignition of the fuel composition is caused by elevated temperature of the air by mechanical compression. Fuel compositions used in compression ignition engines can include, but are not limited to, fuel oils, such as diesel fuels, distillate fuel oils, and residual fuel oils.

Ignition and combustion properties of residual fuel oils can be determined by the method specified in IP 541: Determination of Ignition and Combustion Characteristics of Residual Fuels. In this test method, multiple injections of the residual fuel oil are made into a heated and pressurized combustion chamber of constant volume. The combustion chamber pressure is monitored versus time to determine the various characteristics, including the main combustion delay (MCD). The MCD can be used to calculate an estimated cetane number (ECN). The ECN is generally accepted as an indicator of combustion quality for residual fuel oils. In order to determine, whether a fuel composition can burn in an engine, a minimum cetane number is required. For residual fuel oils, however it can be difficult to measure the MCD, because access to instruments for testing can be limited. Since MCD is used in calculation of ECN, this makes measurement of ECN difficult. Accordingly, the calculated carbon aromaticity index (CCAI) has been developed to predict the ignition quality of residual fuel oils, which is the first part of the overall combustion process.

The CCAI is calculated based on measured density and viscosity properties of residual fuel oils. The formula for calculation of CCAI is found in ISO 8217, Clause 6.2. The CCAI thus can be an indicator of ignition quality for residual fuel oils even where measurement of MCD to provide ECN is unavailable. However, CCAI may not accurately reflect combustion quality of residual fuel oils with low sulfur. With the International Maritime Organization implementing a new global sulfur limit of 0.50 wt. % sulfur, effective Jan. 1, 2020, this is expected to become a more extensive issue.

SUMMARY

Disclosed herein is an example fuel composition having low sulfur content, the fuel composition having the following enumerated properties: a sulfur content of about 0.50% or less by weight of the fuel composition; a calculated carbon aromaticity index of about 870 or less; a density at 15° C. of about 900 kg/m$^3$ to about 1,010 kg/m$^3$; a kinematic viscosity at 50° C. of about 100 centistokes to about 700 centistokes; and an estimated cetane number of about 7 or greater.

Further disclosed herein is an example method of blending fuel compositions. The example method may include blending one or more residual components and one or more petroleum distillate fractions to prepare a fuel composition, wherein the fuel composition has the following enumerated properties: a sulfur content of about 0.50% or less by weight of the fuel composition; a calculated carbon aromaticity index of about 870 or less; a density at 15° C. of about 900 kg/m$^3$ to about 1,010 kg/m$^3$; a kinematic viscosity at 50° C. of about 100 centistokes to about 700 centistokes; and an estimated cetane number of about 7 or greater.

BRIEF DESCRIPTION OF THE DRAWINGS

These drawings illustrate certain aspects of the present disclosure and should not be used to limit or define the disclosure.

The FIGURE illustrates a chart of estimated cetane number (ECN) versus calculated carbon aromaticity index (CCAI).

DESCRIPTION

In various embodiments, the present disclosure may include fuel compositions that are low sulfur and have adequate combustion quality. As used herein, a fuel composition is defined as having "adequate combustion quality" where the fuel composition has an estimated cetane number (ECN) of about 7 or greater. The technique for determining ECN is described in IP 541/06: Determination of Ignition and Combustion Characteristics of Residual Fuels.

As described above, the International Maritime Organization is implementing new standards (commonly referred to as "IMO 2020") requiring development of new marine fuel compositions that are low sulfur to meet the new sulfur requirements that are being implemented on Jan. 1, 2020. In addition to IMO 2020, marine fuel compositions classified as residual marine fuels must meet the requirements of ISO 8217, Fuel Standard Sixth Edition 2017, Table 2, while marine fuel compositions classified as distillate marine fuels must meet the requirements of ISO 8217, Fuel Standard Sixth Edition 2017, Table 1.

To provide fuel compositions that are low sulfur and have adequate combustion quality, embodiments may include blending one or more residual components that are typically higher in sulfur content with one or more petroleum distillate fractions that are typically lower in sulfur content. The additional petroleum distillate fractions may include any number of fractions from a crude refining process. In at least one embodiment, the fuel composition may be classified as a residual marine fuel composition as defined in ISO 8217. Examples of suitable fuel compositions may include a residual component and one or more petroleum distillate fractions such that the fuel compositions have the properties enumerated herein, such as one or more of sulfur content, CCAI, density, kinematic viscosity at about 50° C. ("KV50"), or ECN. In some embodiments, the composition of the components of the fuel compositions and their relative proportions can be selected to provide a fuel composition having the properties enumerated herein.

Embodiments of the fuel compositions may include one or more residual components. The residual components typically include a complex mixture of heavy petroleum components also known in the art as resid, residual, or residuum. The residual components are typically residue from refinery operations, such as distillation or cracking units. In a typical refinery, crude oils can be subjected to atmospheric distillation to produce lighter fractions such as gas oils, kerosene, gasolines, straight run naphtha. etc. Petroleum fractions in the gasoline boiling range, such as naphthas, and those fractions which can readily be thermally or catalytically converted to gasoline boiling range products, such as gas oils, are typically the most valuable product streams in the refinery. The residue from the atmospheric distillation step may then be distilled at a pressure below atmospheric pressure. This later distillation step produces a vacuum gas oil distillate and a vacuum residual oil which typically are substantially cheaper than gas oils. The residual components used in embodiments of the fuel compositions can be the residuals from the atmospheric distillation, vacuum distillation, or other suitable refinery operation.

Examples of suitable residual components may include, but are not limited to, vacuum residuals from fractionating (total/partial) crude oils, atmospheric residuals from fractionating (total/partial) crude oils, visbreaker residuals, FCC bottoms, hydrotreated residual, and deasphalted residuals, among others. Vacuum residuals are the bottoms product from a column under vacuum where the heaviest distilled product is nominally 1050° F. (566° C.). Atmospheric residuals are the bottoms product produced in atmospheric distillation where the endpoint of the heaviest distilled product is nominally 650° F. (343° C.). As used herein, the term "nominally" means here that reasonable experts may disagree on the exact cut point for these terms, but probably by no more than +/−50° F. or at most +/−100° F. Visbreaker residuals are the residuals from thermal cracking processes for increasing yield from atmospheric and vacuum residuals. FCC bottoms are the bottoms product oil from fluid catalytic cracking, including, but not limited to, slurry oil and clarified slurry oil. Combinations of two or more different residual components may also be suitable for use in certain applications. In at least one embodiment, the residual component may include two or more residual components. For example, the residual component may include a first residual component and a second residual component, such as a vacuum residual and an FCC bottoms. One of ordinary skill in the art, with the benefit of this disclosure, should be able to select an appropriate residual component (or combination of residual components) for a particular application.

In some embodiments, the residual component may have a high sulfur content. For example, the residual component may have a sulfur content in wt. % of greater than about 0.10, for example about 0.10 to about 5, about 0.50 to about 3, or about 1 to about 2.5. In some embodiments, the residual component may have a KV50 in centistokes ("cSt") of about 30 or greater, for example about 100 to about 2,500,000, about 1,000 to about 1,000,000, about 2,000 to about 1,000,000, about 100,000 to about 1,000,000, about 600,000 to about 8,000, about 10,000 to about 30,000, about 1,000 to about 5,000, about 100 to about 1,000, or about 100 to about 500. The standardized test method in ISO 3104 (1997) is defined as providing the procedure for determining KV50. In at least one embodiment, the fuel composition may include a first residual component having a higher KV50 and a second residual component having a lower KV50. For example, a first residual component may have a KV50 of about 1,000 to about 1,000,000, about 2,000 to about 2,000,000, about 100,000 to about 1,000,000, about 600,000 to about 8,000, about 10,000 to about 30,000, or about 1,000 to about 5,000, while a second residual component may have a KV50 of about 100 to about 1,000 or about 100 to about 500. By way of further example, the fuel composition may include a vacuum residual having a KV50 of about 1,000 to about 1,000,000, about 2,000 to about 2,000,000, about 100,000 to about 1,000,000, about 600,000 to about 8,000, about 10,000 to about 30,000, or about 1,000 to about 5,000, and a FCC bottoms having a KV50 of about 100 to about 1,000 or about 100 to about 500. One of ordinary skill in the art, with the benefit of this disclosure, should be able to select a KV50 for the residual component (or combinations thereof) for a particular application.

The residual component may be included in the fuel compositions in any suitable concentration, to provide the fuel composition with desirable properties. For example, the residual component may be included in an amount in vol. % of about 1 to about 90, for example, about 1 to about 60, about 1 to about 30, about 10 to about 90, about 10 to about 70, about 10 to about 50, about 10 to about 30, about 20 to about 90, about 20 to about 70, about 20 to about 50, about 30 to about 90 about 30 to about 70, about 30 to about 50, about 40 to about 90, about 40 to about 70, or about 40 to about 50. In some embodiments, the residual component may include a first residual component in an amount in vol. % of about 50 to about 99 and a second residual component in an amount in vol. % of about 1 to about 50. For example, the first residual component may be present in an amount in vol. % of about 50 to about 95, about 60 to about 95, about 70 to about 95, or about 80 to about 95. By way of further example, the second residual component may be present in an amount in vol. % of about 5 to about 50, about 5 to about 40, about 5 to about 30, or about 5 to about 20. One of ordinary skill in the art with the benefit of this disclosure should be able to select an appropriate amount of the residual component to include in the fuel compositions for a particular application.

As previously described, the residual components may be blended with one or more petroleum distillate fractions. The petroleum distillate fractions may include, for example, any of a variety of petroleum fractions obtained from refinery operations. The combustion quality of the distillate component may be defined by the cetane index, as defined by Procedure A in ASTM D4737 (2016)—Standardized Method for Calculated Cetane Index by Four Variable Equation. A distillate component with low combustion quality will have a cetane index of about 8 or less. A distillate component with average combustion quality will have a cetane index of 8 to 29. A distillate component with excellent combustion quality will have a cetane index of about 30 or greater. In at least one embodiment, the fuel composition may include a first petroleum distillate fraction of average combustion quality. In at least one embodiment, the fuel composition may include a second petroleum distillate fraction of excellent combustion quality. In at least one embodiment, the fuel composition may include a first petroleum distillate fraction of average combustion quality and a second petroleum distillate fraction of excellent combustion quality.

In at least one embodiment, the fuel composition may further include a first petroleum distillate fraction. The first petroleum distillate fraction may be defined as having a cetane index of about 8 to about 29, for example, a cetane index of about 8 to about 20, about 8 to about 12, about 12 to about 29, about 18 to about 29, or about 20 to about 29. Thus, the first petroleum distillate fraction may be considered to have average combustion quality. Additional properties that can characterize the first petroleum distillate fraction can include, but are not limited to, density, KV50, and CCAI. In some embodiments, the first petroleum distillate fraction may have a density in kg/m$^3$ of about 850 to about 1,000, for example about 900 to about 1,000, about 900 to about 950, about 900 to about 925, about 925 to about 1,000, about 925 to about 950, about 950 to about 1,000, or about 975 to about 1,000. In some embodiments, the first petroleum distillate fraction may have a KV50 in cSt of about 1 to about 30, for example about 1 to about 20, about 1 to about 10, about 1 to about 5, about 10 to about 20, or about 15 to about 20. In some embodiments, the first petroleum distillate fraction may have a CCAI of 800 to about 1,000, for example, about 800 to about 900, about 800 to about 850, about 850 to about 900, about 900 to about 950, or about 950 to about 1,000. Examples of first petroleum distillate fractions may include any of a variety of petroleum fractions from refinery operations, whether an intermediate or final product, including, but not limited to, light cycle oil, light coker gas oil, heavy cycle oil, heavy coker gas oil, and steam cracked gas oil.

In some embodiments, the first petroleum distillate fraction may have a low sulfur content, such that when blended with the residual component, the fuel composition may be considered IMO 2020 compliant. For example, the first petroleum distillate fraction may have a sulfur content in wt. % of less than about 0.05, for example, about 0.05 to about 0.0001, about 0.1 to about 0.0001, or about 0.001 to about 0.0005.

Where used, the first petroleum distillate fraction may be included in the fuel composition in any suitable amount as desired for a particular application. For example, the first petroleum distillate fraction may be included in the fuel composition in an amount sufficient to provide a lower sulfur content, provide improved combustion quality, or provide both lower sulfur content and improved combustion quality. In some embodiments, the first petroleum distillate fraction may be included in the fuel composition in an amount in vol. % of about 10 to about 60, for example, about 10 to about 50, about 10 to about 40, about 10 to about 30, about 20 to about 60, about 30 to about 60, about 40 to about 60, about 20 to about 50, about 30 to about 50, or about 40 to about 50. In at least one embodiment, the first petroleum distillate fraction may be included in the fuel composition in an amount in vol. % of at least about 25 or greater, at least about 30 or greater, or at least about 35 or greater. One of ordinary skill in the art with the benefit of this disclosure should be able to select an appropriate amount of the first petroleum distillate fraction to include in the fuel compositions for a particular application.

In at least one embodiment, the fuel composition may further include a second petroleum distillate fraction. The second petroleum distillate fraction may be defined as having a cetane index of about 30 or greater, for example, a cetane index of about 30 to about 60, about 40 to about 60, or about 50 to about 60. Thus, the second petroleum distillate fraction may be considered to have excellent combustion quality. Additional properties that can characterize the second petroleum distillate fraction can include, but are not limited to, density, KV50, and CCAI. In some embodiments, the second petroleum distillate fraction may have a density in kg/m$^3$ of about 850 to about 1,000, for example about 850 to about 950, about 850 to about 925, about 850 to about 900, about 850 to about 875, about 900 to about 1,000, or about 950 to about 1,000. In some embodiments, the second petroleum distillate fraction may have a KV50 in cSt of about 1 to about 150, for example, about 1 to about 130, about 1 to about 100, about 1 to about 50, about 1 to about 30, about 1 to about 10, about 5 to about 130, about 5 to about 100, about 5 to about 50, about 5 to about 30, about 5 to about 10, about 10 to about 130, about 10 to about 100, about 10 to about 50, or about 10 to about 30. In some embodiments, the second petroleum distillate fraction may have a CCAI of about 700 to about 900, for example, about 700 to about 850, about 700 to about 800, about 700 to about 750, about 750 to about 900, about 750 to about 850, about 750 to about 800, about 800 to about 900, or about 850 to about 900. Examples of second petroleum distillate fractions may include any of a variety of petroleum fractions from refinery operations, whether an intermediate or final product, including, but not limited to, hydrotreated straight run distillate, hydrocracker distillate, hydrotreated gas oil, heavy vacuum gas oil, light vacuum gas oil, and heavy atmospheric gas oil.

In some embodiments, the second petroleum distillate fraction may have a low sulfur content, such that when blended with the residual component, the fuel composition may be considered IMO 2020 compliant. For example, the second petroleum distillate fraction may have a sulfur content in wt. % of less than about 0.05, for example, about 0.05 to about 0.0001, about 0.1 to about 0.0001, or about 0.001 to about 0.0005.

Where used, the second petroleum distillate fraction may be included in the fuel composition in any suitable amount as desired for a particular application. For example, the second petroleum distillate fraction may be included in the fuel composition in an amount sufficient to provide a lower sulfur content, provide improved combustion quality, or provide both lower sulfur content and improved combustion quality. In some embodiments, the second petroleum distillate fraction may be included in the fuel composition in an amount in vol. % of about 1 to about 50, for example, about 1 to about 40, about 1 to about 30, about 1 to about 20, about 1 to about 10, about 5 to about 50, about 5 to about 40, about 5 to about 30, about 5 to about 20, about 5 to about 10, about 10 to about 50, about 10 to about 40, about 10 to about 30, or about 10 to about 20. In at least one embodiment, the second petroleum distillate fraction may be included in the fuel composition in an amount in vol. % of at least about 10 or greater, at least about 20 or greater, or at least about 30 or greater. One of ordinary skill in the art with the benefit of this disclosure should be able to select an appropriate amount of the second petroleum distillate fraction to include in the fuel compositions for a particular application.

An example fuel composition may include a residual component in an amount of about 50 vol. % to about 80 vol. % and a first petroleum distillate fraction in an amount of about 20 vol. % to about 50 vol. %. The residual component may include any suitable residual component described herein. In at least one embodiment, the residual component may include a vacuum residual. The first petroleum distillate fraction may have a cetane index of about 8 to about 29.

Another example fuel composition may include a first residual component in an amount of about 40 vol. % to about 65 vol. %, a second residual component in an amount of about 5 vol. % to about 20 vol. %, and a first petroleum distillate fraction in an amount of about 15 vol. % to about 55 vol. %. The first residual component may include any suitable residual component described herein. In at least one embodiment, the first residual component may include a vacuum residual. The second residual component may include any suitable residual component described herein. In at least one embodiment, the second residual component may include FCC bottoms. The first petroleum distillate fraction may have a cetane index of about 8 to about 29.

Another example fuel composition may include a residual component in an amount of about 45 vol. % to about 65 vol. %, a first petroleum distillate fraction in an amount of about 30 vol. % to about 40 vol. %, and a second petroleum distillate fraction in an amount of about 5 vol. % to about 25 vol. %. The residual component may include any suitable residual component described herein. In at least one embodiment, the residual component may include a vacuum residual. The first petroleum distillate fraction may have a cetane index from about 8 to about 29. The second petroleum distillate fraction may have a cetane index of about 30 or greater.

Another example fuel composition may include a first residual component in an amount of about 45 vol. % to about 65 vol. %, a second residual component in an amount of about 5 vol. % to about 20 vol. %, and a second petroleum distillate fraction in an amount of about 5 vol. % to about 40 vol. %. The first residual component may include any suitable residual component described herein. In at least one embodiment, the first residual component may include a vacuum residual. The second residual component may include any suitable residual component described herein. In at least one embodiment, the second residual component may include FCC bottoms. The second petroleum distillate fraction may have a cetane index of about 30 or greater.

Another example fuel composition may include a first residual component in an amount of about 40 vol. % to about 60 vol. %, a second residual component in an amount of about 5 vol. % to about 20 vol. %, a first petroleum distillate fraction in an amount of about 10 vol. % to about 40 vol. %, and a second petroleum distillate fraction in an amount of about 5 vol. % to about 30 vol. %. The first residual component may include any suitable residual component described herein. In at least one embodiment, the first residual component may include a vacuum residual. The second residual component may include any suitable residual component described herein. In at least one embodiment, the second residual component may include FCC bottoms. The first petroleum distillate fraction may have a cetane index from about 8 to about 29. The second petroleum distillate fraction may have a cetane index of about 30 or greater.

Various desirable properties for embodiments of the fuel compositions may be specified. Examples of suitable fuel compositions may be enumerated by the following properties: (i) a sulfur content of about 0.50 wt. % or less; (ii) a CCAI value of about 870 or less; (iii) a density at 15° C. of about 900 kg/m$^3$ to about 1010 kg/m$^3$; (iv) a kinematic viscosity at 50° C. ("KV50") of about 100 cSt to about 700 cSt; and (v) an estimated cetane number of about 7 or greater. Fuel compositions with these enumerated properties should have adequate combustion quality while being low sulfur. Even though CCAI alone may not be a predictor of combustion quality, by providing a fuel composition with the preceding enumerated properties, adequate combustion may be provided. In an at least one embodiment, the example fuel compositions may further be enumerated by at least one of the following properties: i) a minimum concentration of 25 vol. % of the first petroleum distillate having a cetane index of about 8 to about 29; or (ii) a minimum concentration of 10 vol. % of the second petroleum distillate having a cetane index of about 30 or greater.

One property that can be used for selection and/or modification of embodiments of the fuel compositions is sulfur content. By way of example, the marine fuel compositions may be considered IMO 2020 compliant in that embodiments of the fuel oil compositions have a sulfur content of about 0.50 wt. % or less. Examples of suitable marine fuel compositions may have a sulfur content in wt. % of about 0.0001 to about 0.50, for example, about 0.0001 to about 0.05, about 0.01 to about 0.1, about 0.05 to about 0.50 or about 0.4 to about 0.5. Specific examples of suitable fuel compositions may have a sulfur content in wt. % of about 0.0001, about 0.001, about 0.005, about 0.01, about 0.02, about 0.03, about 0.05, about 0.1, about 0.2, about 0.3, about 0.4, about 0.45, about 0.49, or about 0.50. One of ordinary skill in the art, with the benefit of this disclosure, should be able to select an appropriate sulfur content for embodiments of the fuel compositions, as desired for a particular application.

Another property that can be used for selection and/or modification of embodiments of the fuel compositions is CCAI. As previously described, CCAI is calculated based on measured density and viscosity properties of a fuel composition. The formula for calculation of CCAI is found in ISO 8217, Clause 6.2. In some embodiments, a fuel composition may have a CCAI of about 870 or less. For example, the fuel compositions may have a CCAI of about 800 to about 870, about 810 to about 870, about 820 to about 870, about 830 to about 870, about 840 to about 870, about 860 to about 870, about 800 to about 860, about 800 to about 850, about 800 to about 840, about 800 to about 830, about 800 to about 820, about 800 to about 810, about 810 to about 860, about 820 to about 860, about 830 to about 860, about 840 to about 860, about 850 to about 860, about 810 to about 850, about 810 to about 840, about 810 to about 830, or about 810 to about 820. Specific examples of suitable fuel compositions may have a CCAI of about 800, about 810, about 820, about 830, about 840, about 850, about 860, or about 870. One of ordinary skill in the art, with the benefit of this disclosure, should be able to select an appropriate CCAI for embodiments of the fuel compositions, as desired for a particular application.

Another property that can be used for selection and/or modification of embodiments of the marine fuel compositions is density. The standardized test method in ISO 3675 (Jun. 15, 1998) is defined as providing the procedure for determination of density. In some embodiments, a fuel composition may have a density at 15° C. in kg/m$^3$ of about 860 to about 1,010. For example, the density at 15° C. of the fuel composition in kg/m$^3$ may be about 860 to about 1,000, about 860 to about 980, about 860 to about 970, about 860 to about 930, about 860 to about 900, about 860 to about 890, about 900 to about 1,010, about 900 to about 950, about 940 to about 1,010, or about 1,000 to about 1,010. Specific examples of suitable marine fuel compositions may have a density at 15° C. in kg/m$^3$ of about 860, about 870, about 880, about 890, about 900, about 910, about 920, about 930, about 940, about 950, about 960, about 970, about 980, about 990, about 1,000, or about 1,010. One of ordinary skill in the art, with the benefit of this disclosure, should be able to select an appropriate density for embodiments of the fuel compositions, as desired for a particular application.

Yet another property that can be used for selection and/or modification of embodiments of the marine fuel compositions is KV50. The standardized test method in ISO 3104 (1997) is defined as providing the procedure for determining KV50. In some embodiments, a fuel composition may have a KV50 in cSt of about 100 to about 700, for example, about 100 to about 650, about 100 to about 600, about 100 to about 550, about 100 to about 500, about 100 to about 450, about 100 to about 400, about 100 to about 350, about 100 to about 300, about 100t to about 250, about 100 to about 200, about 100 to about 150, about 150 to about 700, about 250 to about 700, about 300 to about 700, about 350 to about 700, about 400 to about 700, about 450 to about 700, about 500 to about 700, about 550 to about 700, about 600 to about 700, or about 650 to about 700. Specific examples of suitable marine fuel oil compositions may have a KV50 in cSt of about 100, about 150, about 200, about 250, about 300, about 350, about 380, about 400, about 450, about 500, about 550, about 600, about 650, or about 700. In some embodiments, the fuel composition may have a KV50 in cSt of about 700 or less, about 600 or less, about 400 or less, about 200 or less, or about 100 or less. One of ordinary skill in the art, with the benefit of this disclosure, should be able to select an appropriate KV50 for embodiments of the fuel compositions, as desired for a particular application.

Yet another property that can be used for selection and/or modification of embodiments of the fuel compositions is ECN. As previously described, a fuel composition is defined as having "adequate combustion quality" where the fuel composition has an ECN of about 7 or greater. The technique for determining ECN is described in IP 541: Determination of Ignition and Combustion Characteristics of Residual Fuels. In some embodiments, a fuel composition may have an ECN of about 7 to about 35. For example, the fuel composition may have an ECN of about 7 to about 30, about 7 to about 25, about 7 to about 20, about 7 to about 15, about 7 to about 10, about 10 to about 35, about 15 to about 35, about 20 to about 35, about 25 to about 35, or about 30 to about 35. Specific examples of suitable marine fuel compositions may have an ECN of about 7, about 8, about 9, about 10, about 11, about 12, about 13, about 14, about 15, about 20, about 25, about 30, or about 35. One of ordinary skill in the art, with the benefit of this disclosure, should be able to select an appropriate ECN for embodiments of the fuel compositions, as desired for a particular application.

ECN and CCAI both may be used as a predictor of combustion quality. In some embodiments, ECN and CCAI for a fuel composition may follow a linear trend. However, in some examples, the ECN and CCAI may not follow a linear trend. By way of example, it has been found that CCAI can either under predict the measured ECN or over predict the measured ECN. In these instances, CCAI may not be a good predictor of combustion quality. For example, CCAI may under predict the measured ECN for a fuel composition where the residual component includes a hydrotreated residual material. By way of further example, CCAI may over predict combustion quality for a fuel composition where the residual component has a T50 of about 615° C. or greater and a first petroleum distillate fraction with a density of about 910 kg/m³ or less. T50 is the temperature at which 50 vol % of the sample being distilled has been recovered as condensate, as measured using ASTM D2287. When CCAI over predicts combustion quality, combustion quality of the fuel composition may be controlled, for example, by including average and/or excellent combustion quality distillate fractions in the fuel composition.

Yet another property that can be used for selection and/or modification of embodiments of the fuel compositions is concentration of the first petroleum distillate fraction. The first petroleum distillate fraction may be defined as having a cetane index of from about 8 to about 29, thus being considered to have average combustion quality. By including a sufficient amount of the first petroleum distillate fraction in examples of the fuel compositions, embodiments may provide a fuel composition with adequate combustion quality even where the residual component does not have an adequate combustion quality by itself. In some embodiments, the first petroleum distillate fraction may be included in the fuel composition in an amount in vol. % of at least about 25 or greater, at least about 30 or greater, or at least about 35 or greater. One of ordinary skill in the art with the benefit of this disclosure should be able to select an appropriate amount of the first petroleum distillate fraction to include in the fuel compositions for a particular application.

Yet another property that can be used for selection and/or modification of embodiments of the fuel compositions is concentration of the second petroleum distillate fraction. The second petroleum distillate fraction may be defined as having a cetane index of about 30 or greater, thus being considered to have excellent combustion quality. By including a sufficient amount of the second petroleum distillate fraction in examples of the fuel compositions, embodiments may provide a fuel composition with adequate combustion quality even where the residual component does not have an adequate combustion quality by itself. In some embodiments, the second petroleum distillate fraction may be included in the fuel composition in an amount in vol. % of at least about 10 or greater, at least about 20 or greater, or at least about 30 or greater. One of ordinary skill in the art with the benefit of this disclosure should be able to select an appropriate amount of the second petroleum distillate fraction to include in the fuel compositions for a particular application.

Accordingly, the preceding description describes examples of fuel compositions that are low sulfur and have adequate combustion quality. The compositions and methods disclosed herein may include any of the various features disclosed herein, including one or more of the following embodiments.

Embodiments 1. A fuel composition having low sulfur content, the fuel composition having the following enumerated properties: a sulfur content of about 0.50% or less by weight of the fuel composition; a calculated carbon aromaticity index of about 870 or less; a density at 15° C. of about 900 kg/m³ to about 1,010 kg/m³; a kinematic viscosity at 50° C. of about 100 centistokes to about 700 centistokes; and an estimated cetane number of about 7 or greater.

Embodiment 2. The fuel composition of embodiment 1, wherein the sulfur content is about 0.40 wt. % to about 0.5 wt. %.

Embodiment 3. The fuel composition of embodiment 1 or embodiment 2, wherein the calculated aromaticity index is about 800 to about 870, wherein the density at 15° C. of about 900 kg/m³ to about 1,010 kg/m³ is about 950 kg/km³ to about 1,000 kg/m³, and wherein the kinematic viscosity at 50° C. is about 100 centistokes to about 380 centistokes, and estimated cetane number is about 7 to about 35.

Embodiment 4. The fuel composition of any preceding embodiment, wherein the fuel composition is a residual marine fuel.

Embodiment 5. The fuel composition of any preceding embodiment, wherein the fuel composition comprises a residual component and at least one petroleum distillate fraction.

Embodiment 6. The fuel composition of embodiment 5, wherein the residual component comprises a vacuum residual.

Embodiment 7. The fuel composition of embodiment 5, wherein the residual component comprises a vacuum residual and FCC bottoms.

Embodiment 8. The fuel composition of any one of embodiments 5 to 7, wherein the petroleum distillate fraction is present in an amount of about 25 vol. % of greater and has a cetane index of about 8 to about 29.

Embodiment 9. The fuel composition of any one of embodiments 5 to 7, wherein the petroleum distillate fraction is present in an amount of about 10 vol. % of greater and has a cetane index of about 30 or greater.

Embodiment 10. The fuel composition of any one of embodiments 1 to 4, wherein the fuel composition comprises a residual component in an amount of about 50 vol. % to about 80 vol. % and a petroleum distillate fraction in an amount of about 20 vol. % to about 50 vol. %, wherein the petroleum distillate fraction has a cetane index of from about 8 to about 29.

Embodiment 11. The fuel composition of any one of embodiments 1 to 4, wherein the fuel composition comprises a first residual component in an amount of about 40 vol. % to about 65 vol. %, a second residual component in an amount of about 5 vol. % to about 20 vol. %, and a petroleum distillate fraction in an amount of about 15 vol. % to about 55 vol. %, wherein the petroleum distillate fraction has a cetane index of from about 8 to about 29.

Embodiment 12. The fuel composition of any one of embodiments 1 to 4, wherein the fuel composition comprises a residual component in an amount of about 45 vol. % to about 65 vol. %, a first petroleum distillate fraction in an amount of about 30 vol. % to about 40 vol. %, and a second petroleum distillate fraction in an amount of about 5 vol. % to about 25 vol. %, wherein the first petroleum distillate fraction has a cetane index of about 8 to about 29, and wherein the second petroleum distillate fraction has a cetane index of about 30 or greater.

Embodiment 13. The fuel composition of any one of embodiments 1 to 4, wherein the fuel composition comprises a first residual component in an amount of about 45 vol. % to about 65 vol. %, a second residual component in an amount of about 5 vol. % to about 20 vol. %, and a petroleum distillate fraction in an amount of about 5 vol. % to about 40 vol. %, wherein the petroleum distillate fraction has a cetane index of about 30 or greater.

Embodiment 14. The fuel composition of any one of embodiments 1 to 4, wherein the fuel composition comprises a first residual component in an amount of about 40 vol. % to about 60 vol. %, a second residual component in an amount of about 5 vol. % to about 20 vol. %, a first petroleum distillate fraction in an amount of about 10 vol. % to about 40 vol. %, and a second petroleum distillate fraction in an amount of about 5 vol. % to about 30 vol. %, wherein the first petroleum distillate fraction has a cetane index of about 8 to about 29, and wherein the second petroleum distillate fraction has a cetane index of about 30 or greater.

Embodiment 15. The fuel composition of any one of embodiments 1 to 4, wherein the fuel composition comprises a residual component having a T50 of about 615° C. or greater and a to first distillate fraction having a density of about 910 kg/m³ or less, and wherein the fuel composition is further characterized by at least one of the following: (i) an amount of about 25 vol. % of greater of the first distillate fraction with a cetane index of about 8 to about 29 or (ii) further comprising a second distillate fraction in an amount of about 10 vol. % of greater with a cetane index of about 30 or greater.

Embodiment 16. A method of blending fuel compositions, comprising: blending one or more residual components and one or more petroleum distillate fractions to prepare a fuel composition, wherein the fuel composition has the following enumerated properties: a sulfur content of about 0.50% or less by weight of the fuel composition; a calculated carbon aromaticity index of about 870 or less; a density at 15° C. of about 900 kg/m³ to about 1,010 kg/m³; a kinematic viscosity at 50° C. of about 100 centistokes to about 700 centistokes; and an estimated cetane number of about 7 or greater.

Embodiment 17. The method of embodiment 16, wherein the calculated aromaticity index is about 800 to about 870, wherein the density at 15° C. of about 900 kg/m³ to about 1,010 kg/m³ is about 950 kg/km³ to about 1,000 kg/m³, and wherein the kinematic viscosity at 50° C. is about 100 centistokes to about 380 centistokes, and estimated cetane number is about 7 to about 35.

Embodiment 18. The method of embodiment 16 or embodiment 17, wherein the petroleum distillate fraction comprises at least one of (i) a first distillate fraction in an amount of about 25 vol. % of greater with a cetane index of about 8 to about 29; or (ii) a second distillate fraction in an amount of about 10 vol. % of greater with a cetane index of about 30 or greater.

Embodiment 19. The method of any of embodiments 16 to 18, wherein the one or more residual components comprises a residual component having a T50 of about 615° C. or greater, and wherein one or more petroleum distillate fractions comprises a first distillate fraction having a density of about 910 kg/m³ or less.

Embodiment 20, The method of any one of embodiments 16 to 19, wherein the blending comprises blending an additional distillate fraction in an amount of about 10 vol. % of greater with a cetane index of about 30 or greater to enhance combustion quality of the fuel composition.

EXAMPLES

To facilitate a better understanding of the present disclosure, the following examples of certain aspects of some embodiments are given. In no way should the following examples be read to limit, or define, the entire scope of the disclosure.

Example 1

In this example, the properties of forty-two different sample fuel composition are provided. Of these sample fuel compositions, thirty-six fuel compositions were prepared and measured to obtain the properties, and six fuel compositions are modeled blends with the properties predicted based on the measured properties of the components. The ten fuel compositions that were prepared are listed as Sample Compositions 1-36. The modeled blends are listed as Sample Compositions MB-1 to MB-6. The components were obtained from six different refineries, identified as Refiners A-E.

Table 1 below shows the composition of the sample fuel compositions.

TABLE 1

| Sample | Refinery | Vacuum Residuals Type | Vol % | FCC Bottoms Type | Vol % | First Petroleum Distillate Fraction A Type | Vol % | First Petroleum Distillate Fraction B Type | Vol % | Second Petroleum Distillate Fraction A Type | Vol % | Second Petroleum Distillate Fraction B Type | Vol % |
|---|---|---|---|---|---|---|---|---|---|---|---|---|---|
| 1 | A | VR 1 | 47 | FCC B1 | 18 | HCGO | 13 | — | 0 | GOHF2 | 22 | — | 0 |
| 2 | B | VR 2 | 48 | — | 0 | LCO-4 | 10 | — | 0 | — | 0 | Diesel | 42 |
| 3 | C | VR 3 | 90 | — | 0 | LCO-5 | 10 | — | 0 | — | 0 | — | 0 |
| 4 | C | VR 3 | 75 | — | 0 | LCO-5 | 25 | — | 0 | — | 0 | — | 0 |
| 5 | C | VR 4 | 65 | — | 0 | LCO-5 | 35 | — | 0 | — | 0 | — | 0 |
| 6 | C | VR 4 | 90 | — | 0 | LCO-6 | 10 | — | 0 | — | 0 | — | 0 |
| 7 | C | VR 4 | 75 | — | 0 | LCO-6 | 25 | — | 0 | — | 0 | — | 0 |
| 8 | C | VR 4 | 65 | — | 0 | LCO-6 | 35 | — | 0 | — | 0 | — | 0 |
| 9 | A | VR 1 | 64 | — | 0 | SCGO | 36 | — | 0 | — | 0 | — | 0 |
| 10 | D | VR 5 | 76.8 | — | 0 | SCGO | 2 | — | 0 | 2$^{nd}$ Dist. Blend A | 21.2 | — | 0 |
| 11 | D | VR 5 | 67.3 | — | 0 | SCGO | 12 | — | 0 | 2$^{nd}$ Dist. Blend B | 20.7 | — | 0 |
| 12 | D | VR 5 | 69.1 | — | 0 | SCGO | 22.6 | — | 0 | 2$^{nd}$ Dist. Blend C | 8.3 | — | 0 |
| 13 | D | VR 5 | 49.2 | — | 0 | SCGO | 39.6 | — | 0 | 2$^{nd}$ Dist. Blend D | 11.2 | — | 0 |
| 14 | B | VR 6 | 28 | — | 0 | — | 0 | — | 0 | VGO 1 | 65 | Diesel | 10 |
| 15 | B | VR 6 | 41 | — | 0 | — | 0 | — | 0 | VGO 1 | 47 | Diesel | 12 |
| 16 | B | VR 7 | 16.4 | — | 0 | — | 0 | — | 0 | VGO 2 | 64.7 | Diesel | 18.9 |
| 17 | B | VR 6 | 80 | — | 0 | — | 0 | — | 0 | VGO 1 | 20 | — | 0 |
| 18 | B | VR 2 | 53 | — | 0 | — | 0 | — | 0 | VGO 3 | 25 | Diesel | 22 |
| 19 | B | VR 2 | 58 | — | 0 | — | 0 | — | 0 | HC Btms | 42 | — | 0 |
| 20 | A | VR 1 | 53 | FCC B1 | 9 | — | 0 | — | 0 | GOHF2 | 38 | — | 0 |
| 21 | A | VR 8 | 42 | FCC B4 | 30 | — | 0 | — | 0 | GOHF2 | 28 | — | 0 |
| 22 | C | VR 3 | 65 | — | 0 | — | 0 | — | 0 | HAGO-1 | 35 | — | 0 |
| 23 | C | VR 3 | 80 | — | 0 | — | 0 | — | 0 | HAGO-1 | 20 | — | 0 |
| 24 | C | VR 3 | 70 | — | 0 | — | 0 | — | 0 | MGO | 30 | — | 0 |
| 25 | C | VR 3 | 65 | — | 0 | GO | 35 | — | 0 | — | 0 | — | 0 |
| 26 | C | VR 3 | 92 | — | 0 | — | 0 | — | 0 | HAGO-1 | 8 | — | 0 |
| 27 | C | VR 3 | 80 | — | 0 | GO | 20 | — | 0 | — | 0 | — | 0 |
| 28 | E | VR 9 | 45 | — | 0 | HHO | 55 | — | 0 | — | 0 | — | 0 |
| 29 | A | VR 1 | 43 | FCC B1 | 15 | LCO-1 | 2 | HCGO | 40 | — | 0 | — | 0 |
| MB-1 | A | VR 1 | 60 | — | 0 | LCO-1 | 30 | — | 0 | GOHF2 | 10 | — | 0 |
| 30 | A | VR 1 | 50 | FCC B4 | 22 | LCO-1 | 13 | — | 0 | GOHF2 | 15 | — | 0 |
| 31 | A | VR 1 | 75 | — | 0 | LCO-1 | 25 | — | 0 | — | 0 | — | 0 |
| MB-2 | A | VR 1 | 70 | — | 0 | LCO-1 | 30 | — | 0 | — | 0 | — | 0 |
| MB-3 | A | VR 1 | 60 | FCC B1 | 10 | LCO-1 | 30 | — | 0 | — | 0 | — | 0 |

TABLE 1-continued

| Sample | Refinery | Vacuum Residuals Type | Vol % | FCC Bottoms Type | Vol % | First Petroleum Distillate Fraction A Type | Vol % | First Petroleum Distillate Fraction B Type | Vol % | Second Petroleum Distillate Fraction A Type | Vol % | Second Petroleum Distillate Fraction B Type | Vol % |
|---|---|---|---|---|---|---|---|---|---|---|---|---|---|
| 32 | F | 70% VR 10 + 30% HCO 3 | 49 | FCC B2 | 5 | LCO-3 | 2.3 | HCO-3 | 23.7 | LVGO | 5 | HAGO-2 | 15 |
| 33 | F | 70% VR 11 + 30% HCO 3 | 50.4 | FCC B2 | 5 | LCO-3 | 5.98 | HCO-3 | 28.62 | LVGO | 10 | — | 0 |
| 34 | F | 70% VR 10 + 30% HCO 3, 18-36492) | 50.4 | FCC B2 | 5 | LCO-3 | 5.98 | HCO-3 | 28.62 | LVGO | 10 | — | 0 |
| 35 | F | 70% VR 11 + 30% HCO 3 | 54.6 | — | 0 | LCO-3 | 10.12 | HCO-3 | 35.28 | — | 0 | — | 0 |
| 36 | F | 70% VR 11 + 30% HCO 3 | 54.6 | FCC B2 | 10 | LCO-3 | 5.52 | HCO-3 | 29.88 | — | 0 | — | 0 |
| MB-4 | F | 70% VR 11 + 30% HCO 3 | 49 | FCC B2 | 5 | LCO-3 | 9.2 | HCO-3 | 31.8 | LVGO | 5 | — | 0 |
| MB-5 | F | 70% VR 11 + 30% HCO 3 | 52.5 | — | 0 | LCO-3 | 11.5 | HCO-3 | 36 | — | 0 | — | 0 |
| 37 | E | VR 8 | 80 | — | 0 | HHO | 20 | — | 0 | — | 0 | — | 0 |
| 38 | F | VR 8 | 50 | FCC B3 | 15 | HHO | 35 | — | 0 | — | 0 | — | 0 |
| MB-6 | F | 70% VR 11 + 30% HCO 3 | 49 | FCC B2 | 5 | LCO-3 | 11.5 | HCO-3 | 34.5 | — | 0 | — | 0 |

The 21.2 vol % of the 2$^{nd}$ Distillate Blend A contains 0.9 vol % FLUX 1, 4.0 vol % FLUX 2 bottoms, 8.1 vol % FLUX 3 bottoms, 1.3 vol % FLUX 4, and 6.8 vol % FLUX 5

The 20.7 vol % of the 2$^{nd}$ Distillate Blend B contains 0.9 vol % FLUX 1, 4.0 vol % FLUX 2 bottoms, 7.9 vol % FLUX 3 bottoms, 1.3 vol % FLUX 4, and 6.7 vol % FLUX 5.

The 8.3 vol % of the 2$^{nd}$ Distillate Blend C contains 0.4 vol % FLUX 1, 1.6 vol % FLUX 2 bottoms, 3.2 vol % FLUX 3 bottoms, 0.5 vol % FLUX 4, and 2.7 vol % FLUX 5.

The 11.2 vol % of the 2$^{nd}$ Distillate Blend D contains 0.5 vol % FLUX 1, 2.1 vol % FLUX 2 bottoms, 4.3 vol % FLUX 3 bottoms, 0.7 vol % FLUX 4, and 3.6 vol % FLUX 5.

Table 2 below shows the composition of the sample fuel compositions.

TABLE 2

| Sample | Refinery | Density, kg/m3 | KV50, cSt | CCAI | ECN |
|---|---|---|---|---|---|
| 1 | A | 966.8 | 346 | 829 | 24.2 |
| 2 | B | 901.8 | 29.5 | 790 | 38 |
| 3 | C | 956.1 | 255 | 822 | 30.4 |
| 4 | C | 948.1 | 69.9 | 830 | 27.6 |
| 5 | C | 964.8 | 60 | 849 | 16.2 |
| 6 | C | 989.6 | 739.1 | 845 | 17.1 |
| 7 | C | 982.5 | 151.8 | 854 | 14.7 |
| 8 | C | 977.6 | 69 | 860 | 13.6 |
| 9 | A | 994.8 | 141 | 866 | 8.0 |
| 10 | D | 949.3 | 215.3 | 816 | 24.7 |

TABLE 2-continued

| Sample | Refinery | Density, kg/m3 | KV50, cSt | CCAI | ECN |
|---|---|---|---|---|---|
| 11 | D | 949.2 | 72.03 | 830 | 20.9 |
| 12 | D | 973 | 86.1 | 851 | 16 |
| 13 | D | 970.1 | 19.97 | 872 | 12.9 |
| 14 | B | 908.4 | 67.1 | 790 | 52 |
| 15 | B | 908.3 | 66.6 | 790 | 50 |
| 16 | B | 915.4 | 23.3 | 814 | 50 |
| 17 | B | 927.3 | 352.2 | 789 | 45 |
| 18 | B | 902 | 30.9 | 789 | 41 |
| 19 | B | 925.8 | 49.4 | 805 | 27.8 |
| 20 | A | 953.9 | 362 | 815 | 29.6 |
| 21 | A | 997.3 | 1152 | 847 | 11.1 |
| 22 | C | 958.9 | 352.7 | 821 | 37.6 |
| 23 | C | 971.1 | 809.9 | 825 | 30 |
| 24 | C | 942.5 | 118.8 | 817 | 35.2 |
| 25 | C | 979.2 | 849.9 | 833 | 27.7 |
| 26 | C | 944.8 | 2233 | 790 | 23.7 |
| 27 | C | 982.7 | 1400 | 832 | 22.7 |
| 28 | E | 975.9 | 44.64 | 867 | 31.4 |
| 29 | A | 980.7 | 525 | 838 | 16.7 |
| MB-1 | A | 983.5 | 153 | 855 | 12 |
| 30 | A | 985.2 | 470.8 | 843 | 10.9 |
| 31 | A | 979.1 | 741 | 834 | 7.9 |
| MB-2 | A | 1000.8 | 485 | 859 | 7 |
| MB-3 | A | 999.8 | 269 | 864 | 7 |
| 32 | F | 969.9 | 286 | 834 | 17.8 |
| 33 | F | 978.4 | 1259 | 828 | 14.2 |
| 34 | F | 976.6 | 235 | 843 | 12.4 |
| 35 | F | 945.1 | 1738 | 792 | 12.3 |
| 36 | F | 957.3 | 4885 | 796 | 10.3 |
| MB-4 | F | 981.1 | 301 | 845 | 9 |
| MB-5 | F | 980.4 | 283 | 844 | 7 |
| 37 | E | 954.2 | 245 | 819 | 43 |
| 38 | F | 983.4 | 80 | 863 | 22.8 |
| MB-6 | F | 984.1 | 247 | 850 | 7 |

The FIGURE is a plot of measured or predicted ECN versus calculated CCAI for the sample compositions of Tables 1 and 2. While, the sample compositions of Table 1 meet most of the ISO 8217 specifications, including CCAI, the FIGURE illustrates that the ECN values reveal a range of ECN values for similar CCAI values, thus indicating the CCAI alone may not guarantee adequate combustion quality of a residual fuel composition.

Typically, ECN and CCAI follow a linear trend. We have found examples where the trend is not linear. Either CCAI under predicts the measured ECN (Class B) or the CCAI over predicts the measured ECN (Class C). The latter class is potentially problematic because the CCAI may falsely indicate that the fuel oil has acceptable combustion quality. Class B is defined as a fuel oil containing hydrotreated residual material (e.g., see VR9). Class C is defined as a fuel oil containing a residual material with a T50 of 615° C. or greater and a first petroleum distillate fraction with a density of 910 kg/m³ or less. When the fuel oil blend meets the characteristics of Class C, the combustion should be measured by ECN. In the absence of measuring ECN, the combustion quality of the blend can be controlled by including either a larger amount of the first petroleum distillate fraction or a larger amount of the second petroleum distillate fraction as compared to the initial blend recipe.

Table 3 below shows the measured properties of the vacuum residuals used in the sample compositions provided in Table 1 above. Eleven different vacuum residuals were used in the sample compositions indicated as VR1 to VR 11. The properties indicated in Table 3 below for VR10 and VR11 are for a mixture of 70 vol. % of a vacuum residual and 30 vol. % of HCO-3. The boiling point ranges in the table below (and following tables) were measured in accordance with ASTM D2287 for a simulated distillation. The resid T90 for certain Vacuum Residuals are not reported in Table 3 below as the samples were above the upper temperature limit of the test method (i. e., "adl").

TABLE 3

| Vacuum Residuals | resid density, kg/m3 | resid KV100, cSt | resid CCAI | resid T10, deg C. | resid T50, deg C. | resid T90, deg C. |
|---|---|---|---|---|---|---|
| VR 1 | 1004 | 3710 | 815 | 569.4 | 659.4 | adl |
| VR 2 | 971.5 | 98.599 | 818 | n/a | n/a | adl |
| VR 3 | 987.2 | 119 | 831 | 442.2 | 568.8 | 733.3 |
| VR 4 | 995.9 | 111.5 | 841 | 432.7 | 560 | adl |
| VR 5 | 977.9 | 131.9 | 821 | 455.5 | 613.3 | 721.7 |
| VR 6 | 932.8 | 47.474 | 789 | 324 | 610 | 731 |
| VR 7 | 973.2 | 48.425 | 830 | 325 | 581 | 727 |
| VR 8 | 993 | 2326 | 807 | 605 | 702 | adl |
| VR 9 | 940.6 | 43.49 | 799 | 387.7 | 456.7 | 541.7 |
| VR 10 (vac resid + 30% HCO-3) | 989.5 | 115.3 | 834 | 307.2 | 621.7 | 725.5 |
| VR 11 (vac resid + 30% HCO-3) | 991.6 | 1137 | 812 | 551.7 | 637.2 | 719.4 |

Table 4 below shows the measured properties of the FCC bottoms components used in the sample compositions provided in Table 1 above. Four different FCC bottoms components were used in the sample compositions indicated as FCCB1, FCCB2, FCCB3, and FCCB4.

TABLE 4

| FCC Bottoms | Density (kg/m³) | KV50 (cSt) | CCAI | ECN | T10, ° C. | T50, ° C. | T90, ° C. |
|---|---|---|---|---|---|---|---|
| FCCB1 | 1000 | 139.5 | 872 | 19.8 | 386 | 443 | 509 |
| FCCB2 | 1066 | 467.2 | 925 | 7.7 | 356 | 420 | 531 |
| FCCB3 | 1077 | 418 | 937 | not tested | 309 | 431 | 541 |
| FCCB4 | 1080 | 3586 | 921 | 5.6 | 404 | 466 | 533 |

Table 5 below shows the measured properties of the first petroleum distillate fraction used in the sample compositions provided in Table 1 above. As indicated, a number of different petroleum distillate fractions were used, including: light cycle oil (LCO); heavy cycle oil (HCO); a mixture of light cycle oil and heavy cycle oil (LCO+HCO); heavy cracked gas oil (HCGO); gas oil (GO), heavy heating oil (HHO); and steam cracked gas oil (SCGO).

TABLE 5

| First Petroleum Distillate Fraction | Density (kg/m³) | KV50 (cSt) | CCAI | ECN | T10, ° C. | T50, ° C. | T90, ° C. | Cetane Index |
|---|---|---|---|---|---|---|---|---|
| LCO-1 | 909.4 | 1.8 | 879 | 7.1 | 191 | 257 | 318 | 24.4 |
| HCO-1 | 987.4 | 4.1 | 929 | 3 | 244 | 302 | 356 | 15.0 |
| LCO-2 46% + HCO-2 54% | 946.6 | 1.9 | 914 | 4 | 194 | 257 | 334 | 20.9 |

TABLE 5-continued

| First Petroleum Distillate Fraction | Density (kg/m³) | KV50 (cSt) | CCAI | ECN | T10, °C. | T50, °C. | T90, °C. | Cetane Index |
|---|---|---|---|---|---|---|---|---|
| LCO-3, avg | 904.7 | 1.3 | 891 | Not tested | 201 | 230 | 256 | 19.8 |
| HCO-3, avg | 983.3 | 4.6 | 921 | Not tested | 288 | 310 | 353 | 20.6 |
| HCGO | 945.9 | 11.2 | 860 | 34.3 | 309 | 372 | 414 | 29.0 |
| GO | 964.3 | 143 | 836 | 35.7 | 377 | 467 | 573 | 25.7 |
| LCO-4 | 942.0 | 2.3 | Not tested | Not tested | Not tested | Not tested | Not tested | Not tested |
| LCO-5 | 908.7 | 1.7 | 882 | Not tested | 203 | 246 | 312 | 27.2 |
| LCO-6 | 946.6 | 2.1 | 848 | Not tested | 238 | 270 | 312 | 20.8 |
| HHO | 1004 | 8.3 | 925 | Not tested | 263 | 343 | 403 | 13.0 |
| SCGO | 998.5 | 2.0 | 966 | 0 | 220 | 241 | 277 | 8.7 |

Table 6 below shows the measured properties of the second petroleum distillate component used in the sample compositions provided in Table 1 above. As indicated, the following petroleum distillate fractions were used: hydrofined gas oil (GOHF2); vacuum gas oil (VGO); heavy vacuum gas oil (HVGO); hydrocracker bottoms (HC Btms); light vacuum gas oil (LVGO); heavy atmospheric gas oil (HAGO); marine gas oil (MGO); and flux.

TABLE 5

| Second Petroleum Distillate Fraction | Density (kg/m³) | KV50 (cSt) | CCAI | ECN | T10, °C. | T50, °C. | T90, °C. | Cetane Index |
|---|---|---|---|---|---|---|---|---|
| GOHF2-1 | 867 | 4.75 | 804 | 58 | 244 | 332 | 386 | 48.1 |
| GOHF2-2 | 887 | 5.6 | 819 | 53 | 280 | 334 | 384 | 47.5 |
| Diesel | 839 | 1.9 | 808 | Not tested | 201 | 251 | 324 | 47.2 |
| VGO 1 | 906.8 | 64.3 | 789 | Not tested | 339 | 466 | 632 | 30.4 |
| VGO 2 | 923.6 | 48.2 | 810 | Not tested | 321 | 430 | 516 | 36.1 |
| VGO 3 | 860.7 | 3.9 | 804 | Not tested | 271 | 311 | 346 | 54.7 |
| HC Btms | 891.4 | 3.1 | 842 | Not tested | 254 | 296 | 357 | 40.5 |
| HAGO-1 | 906.3 | 25.7 | 804 | Not tested | 343 | 418 | 499 | 49.3 |
| MGO | 847.7 | 2.9 | 801 | Not tested | 187 | 298 | 372 | 50.3 |
| FLUX 1 | 772.8 | 1.0 | 973 | Not tested | 174 | 194 | 208 | 57.1 |
| FLUX 2 bottoms | 804.5 | 2.4 | 916 | Not tested | 228 | 256 | 291 | 65.8 |
| FLUX 3 bottoms | 779.7 | 1.2 | 948 | Not tested | 177 | 197 | 257 | 55.0 |
| FLUX 4 | 792.5 | 1.6 | 769 | Not tested | 182 | 195 | 242 | 48.6 |
| FLUX 5 | 866.2 | 7.3 | 791 | Not tested | 286 | 333 | 403 | 57.0 |
| LVGO | 888 | 9.929 | 805 | 57 | 286 | 347 | 388 | 45.5 |
| HAGO-2 | 878.7 | 11.17 | 793 | 65 | 302 | 359 | 396 | 52.6 |

While the disclosure has been described with respect to a number of embodiments and examples, those skilled in the art, having benefit of this disclosure, will appreciate that other embodiments can be devised which do not depart from the scope and spirit of the disclosure as disclosed herein. Although individual embodiments are discussed, the present disclosure covers all combinations of all those embodiments.

While compositions, methods, and processes are described herein in terms of "comprising," "containing," "having," or "including" various components or steps, the compositions and methods can also "consist essentially of" or "consist of" the various components and steps. The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of the disclosure, additionally, they do not exclude impurities and variances normally associated with the elements and materials used.

All numerical values within the detailed description and the claims herein modified by "about" or "approximately" with respect to the indicated value are intended to take into account experimental error and variations that would be expected by a person having ordinary skill in the art.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited.

The invention claimed is:

1. A fuel composition having low sulfur content comprising from 10 vol % to 90 vol % of at least one petroleum distillate fraction having a cetane index of at least 8 and a residual component at from 10 vol % to 90 vol %, the fuel composition having the following enumerated properties:
   a sulfur content of about 0.50% or less by weight of the fuel composition;
   a calculated carbon aromaticity index of about 870 or less;
   a density at 15° C. of about 900 kg/m$^3$ to about 1,010 kg/m$^3$;
   a kinematic viscosity at 50° C. of about 100 centistokes to about 700 centistokes; and
   an estimated cetane number of about 7 to about 13.

2. The fuel composition of claim 1, wherein the sulfur content is about 0.40 wt. % to about 0.5 wt. %.

3. The fuel composition of claim 1, wherein the calculated aromaticity index is about 800 to about 870, wherein the density at 15° C. is about 950 kg/km$^3$ to about 1,000 kg/m$^3$, wherein the kinematic viscosity at 50° C. is about 100 centistokes to about 380 centistokes, and wherein the estimated cetane number is about 7 to about 10.

4. The fuel composition of claim 1, wherein the fuel composition is a residual marine fuel.

5. The fuel composition of claim 1, wherein the residual component comprises a vacuum residual.

6. The fuel composition of claim 1, wherein the residual component comprises a vacuum residual and FCC bottoms.

7. The fuel composition of claim 1, wherein the at least one petroleum distillate fraction is present in an amount of about 25 vol. % or greater and has a cetane index of about 8 to about 29.

8. The fuel composition of claim 1, wherein the at least one petroleum distillate fraction is present in an amount of about 10 vol. % or greater and has a cetane index of about 30 or greater.

9. The fuel composition of claim 1, wherein the fuel composition comprises a residual component in an amount of about 50 vol. % to about 80 vol. % and a petroleum distillate fraction in an amount of about 20 vol. % to about 50 vol. %, wherein the petroleum distillate fraction has a cetane index of from about 8 to about 29.

10. The fuel composition of claim 1, wherein the fuel composition comprises a first residual component in an amount of about 40 vol. % to about 65 vol. %, a second residual component in an amount of about 5 vol. % to about 20 vol. %, and a petroleum distillate fraction in an amount of about 15 vol. % to about 55 vol. %, wherein the petroleum distillate fraction has a cetane index of from about 8 to about 29.

11. The fuel composition of claim 1, wherein the fuel composition comprises a residual component in an amount of about 45 vol. % to about 65 vol. %, a first petroleum distillate fraction in an amount of about 30 vol. % to about 40 vol. %, and a second petroleum distillate fraction in an amount of about 5 vol. % to about 25 vol. %, wherein the first petroleum distillate fraction has a cetane index of about 8 to about 29, and wherein the second petroleum distillate fraction has a cetane index of about 30 or greater.

12. The fuel composition of claim 1, wherein the fuel composition comprises a first residual component in an amount of about 45 vol. % to about 65 vol. %, a second residual component in an amount of about 5 vol. % to about 20 vol. %, and a petroleum distillate fraction in an amount of about 5 vol. % to about 40 vol. %, wherein the petroleum distillate fraction has a cetane index of about 30 or greater.

13. The fuel composition of claim 1, wherein the fuel composition comprises a first residual component in an amount of about 40 vol. % to about 60 vol. %, a second residual component in an amount of about 5 vol. % to about 20 vol. %, a first petroleum distillate fraction in an amount of about 10 vol. % to about 40 vol. %, and a second petroleum distillate fraction in an amount of about 5 vol. % to about 30 vol. %, wherein the first petroleum distillate fraction has a cetane index of about 8 to about 29, and wherein the second petroleum distillate fraction has a cetane index of about 30 or greater.

14. The fuel composition of claim 1, wherein the fuel composition comprises a residual component having a T50 of about 615° C. or greater and a first distillate fraction having a density of about 910 kg/m$^3$ or less, and wherein the fuel composition is further characterized by at least one of the following: (i) an amount of about 25 vol. % or greater of the first distillate fraction with a cetane index of about 8 to about 29 or (ii) further comprising a second distillate fraction in an amount of about 10 vol. % or greater with a cetane index of about 30 or greater.

15. A method of blending fuel compositions, comprising:
   blending at from 10 vol % to 90 vol % of one or more residual components and one or more petroleum distillate fractions to prepare a fuel composition, wherein the fuel composition includes from 10 vol % to 90 vol % of the one or more petroleum distillate fractions having a cetane index of at least 8, wherein the fuel composition has the following enumerated properties:
   a sulfur content of about 0.50% or less by weight of the fuel composition;
   a calculated carbon aromaticity index of about 870 or less;
   a density at 15° C. of about 900 kg/m$^3$ to about 1,010 kg/m$^3$;
   a kinematic viscosity at 50° C. of about 100 centistokes to about 700 centistokes; and
   an estimated cetane number of about 7 to about 13.

16. The method of claim 15, wherein the calculated aromaticity index is about 800 to about 870, wherein the density at 15° C. is about 950 kg/km$^3$ to about 1,000 kg/m$^3$, and wherein the kinematic viscosity at 50° C. is about 100 centistokes to about 380 centistokes, and estimated cetane number is about 7 to about 13.

17. The method of claim 15, wherein the petroleum distillate fraction comprises at least one of (i) a first distillate fraction in an amount of about 25 vol. % or greater with a cetane index of about 8 to about 29; or (ii) a second distillate fraction in an amount of about 10 vol. % or greater with a cetane index of about 30 or greater.

18. The method of claim 15, wherein the one or more residual components comprises a residual component having a T50 of about 615° C. or greater, and wherein one or more petroleum distillate fractions comprises a first distillate fraction having a density of about 910 kg/m$^3$ or less.

19. The method of claim 15, wherein the blending comprises blending an additional distillate fraction in an amount of about 10 vol. % or greater with a cetane index of about 30 or greater to enhance combustion quality of the fuel composition.

\* \* \* \* \*